(12) United States Patent
Pu

(10) Patent No.: US 12,307,657 B2
(45) Date of Patent: May 20, 2025

(54) SYSTEM AND METHOD FOR QUANTIFYING THE EXTENT OF DISEASE FROM 2-D IMAGES

(71) Applicant: UNIVERSITY OF PITTSBURGH—OF THE COMMONWEALTH SYSTEM OF HIGHER EDUCATION, Pittsburgh, PA (US)

(72) Inventor: Jiantao Pu, Sewickley, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 786 days.

(21) Appl. No.: 17/348,840

(22) Filed: Jun. 16, 2021

(65) Prior Publication Data

US 2022/0084193 A1    Mar. 17, 2022

Related U.S. Application Data

(60) Provisional application No. 63/078,512, filed on Sep. 15, 2020.

(51) Int. Cl.
*G06T 7/00* (2017.01)
*G06N 3/088* (2023.01)
(Continued)

(52) U.S. Cl.
CPC ........... *G06T 7/0012* (2013.01); *G06N 3/088* (2013.01); *G16H 10/60* (2018.01); *G16H 30/40* (2018.01);
(Continued)

(58) Field of Classification Search
CPC . G06N 3/08; G06N 3/09; G16H 50/20; G06T 7/0012; G06T 7/0014
See application file for complete search history.

(56) References Cited

U.S. PATENT DOCUMENTS

2015/0238270 A1* 8/2015 Raffy .................... A61B 90/37
600/407
2018/0061058 A1* 3/2018 Xu ......................... G06N 3/084
(Continued)

OTHER PUBLICATIONS

Filippo Arcadu, Fethallah Benmansour, Andreas Maunz, John Michon, Zdenka Haskova, Dana McClintock, Anthony P. Adamis, Jeffrey R. Willis, Marco Prunotto; Deep Learning Predicts OCT Measures of Diabetic Macular Thickening From Color Fundus Photographs. Invest. Ophthalmol. Vis. Sci. 2019;60(4):852-857. doi: https://doi.org/10.1167/iovs.18-25634.

(Continued)

Primary Examiner — Wen W Huang
(74) Attorney, Agent, or Firm — Philip E. Levy; Eckert Seamans Cherin & Mellott, LLC

(57) ABSTRACT

A disease assessment method includes using a machine learning system and 2-D image data to quantify an extent of disease in the patient, wherein the machine learning system has been previously trained using 3-D image data for each of a plurality of 3-D images obtained from a plurality of subjects, and 2-D image data for each of a plurality of 2-D images obtained from the plurality of subjects, wherein each of the 2-D images is associated with a corresponding one of the 3-D images and is captured at the same time as the corresponding one of the 3-D images or within a certain predetermined time frame of capturing the corresponding one of the 3-D images, and wherein a ground truth for the 2-D images comprises for each of the 3-D images a quantification of an extent of the predetermined disease based on the 3-D image data for the 3-D image.

39 Claims, 2 Drawing Sheets

(51) Int. Cl.
  *G16H 10/60* (2018.01)
  *G16H 30/40* (2018.01)
  *G16H 50/20* (2018.01)

(52) U.S. Cl.
  CPC ... *G16H 50/20* (2018.01); *G06T 2207/30061* (2013.01)

(56) References Cited

U.S. PATENT DOCUMENTS

2019/0295709 A1* 9/2019 Chabin ............... G06T 7/0012
2020/0380680 A1* 12/2020 Aoyagi ............... G06V 10/772
2021/0192279 A1* 6/2021 Laaksonen ............ G16H 30/20
2021/0398654 A1* 12/2021 Chaganti ............... G16H 50/80
2022/0157048 A1* 5/2022 Ting ..................... G06V 10/82
2022/0384035 A1* 12/2022 Shi ..................... G06V 10/774

OTHER PUBLICATIONS

Varadarajan, A.V., Bavishi, P., Ruamviboonsuk, P. et al. Predicting optical coherence tomography-derived diabetic macular edema grades from fundus photographs using deep learning. Nat Commun 11, 130 (2020). https://doi.org/10.1038/s41467-019-13922-8.

Pu, J., Sechrist, J., Meng, X., Leader, J.K. and Sciurba, F. (2021), A pilot study: quantify lung vol. and emphysema extent directly from 2-D scout images. Medical Physics. Accepted Author Manuscript. https://doi.org/10.1002/mp. 15019.

* cited by examiner

SYSTEM AND METHOD FOR QUANTIFYING THE EXTENT OF DISEASE FROM 2-D IMAGES

CROSS-REFERENCE TO RELATED APPLICATIONS

This application claims priority under 35 U.S.C. § 119(e) from U.S. provisional patent application No. 63/078,512, titled "System and Method for Quantifying the Extent of Disease From 2-D Images" and filed on Sep. 15, 2020, the contents of which are incorporated herein by reference.

GOVERNMENT CONTRACT

This invention was made with government support under grant #s CA237277 and HL096613 awarded by the National Institutes of Health (NIH). The government has certain rights in the invention.

BACKGROUND OF THE INVENTION

1. Field of the Invention

The present invention relates to a system and method for assessing the extent/progression of a disease, such as, without limitation, emphysema, and in particular to a machine learning system and method for quantifying the extent of a disease, such as emphysema, based on 2-D images, such as 2-D x-ray images.

2. Description of the Related Art

Lung disease, such as pneumonia and chronic obstructive pulmonary disease (COPD), is a leading cause of disability and death in the United States and worldwide. As a result, a large number of investigations have been performed to quantitatively assess the extent of lung disease and its morphological characteristics using volumetric imaging, such as chest CT. However, due to resource limitations, cost, and radiation exposure concerns, CT imaging is not typically ordered in clinical practice to confirm a clinician's suspicion for lung disease and/or to assess disease extent.

As compared with CT and other more advanced imaging techniques, two-dimensional (2-D) imaging modalities, such as chest x-ray radiography (CXR), is more often used in clinical practice to non-invasively diagnose the presence of lung disease (e.g., pneumonia and emphysema). 2-D CXR imaging has the advantage of being widely available due to lower technical needs, portability, and the fact that it is less expensive than other imaging modalities. However, as a two-dimensional (2-D) imaging method. CXR visualizes the projection of the disease superimposed on other anatomical structures, resulting in an often ambiguous depiction of lung abnormalities. Consequently, the sensitivity of 2-D CXR to detect the presence of emphysema is suboptimal, and its capability of quantifying the burden of emphysema is limited.

A significant amount of research has been dedicated to developing computer tools to facilitate the detection and diagnosis of a variety of lung diseases depicted on CXR images in an effort to improve radiologists' performance and ease some of their workloads. Recent use of deep learning technology, namely convolutional neural network (CNN) technology, has demonstrated remarkable performance for other areas of medical image analysis. Most investigations leveraged publicly available CXR datasets that only have bimodal subjective disease positive or negative diagnostic information. In the ground truth, the disease type and location are manually labeled by radiologists using a bounding box. Significant time- and cost-consuming efforts are typically required for human experts to manually label the images and compute quantitative metrics (e.g., volume) to generate "ground-truth", yet even in these cases its accuracy and consistency may be in question due to human variation.

SUMMARY OF THE INVENTION

In one embodiment, a method of training a predictive matching learning system for disease assessment is provided. The method includes receiving in a computer system (i) 3-D image data for each of a plurality of 3-D images obtained from a plurality of subjects, and (ii) 2-D image data for each of a plurality of 2-D images obtained from the plurality of subjects, wherein each of the 2-D images is associated with a corresponding one of the 3-D images and is captured at the same time as the corresponding one of the 3-D images or within a certain predetermined time frame of capturing the corresponding one of the 3-D images. The method further includes, for each of the 3-D images, determining in the computer system a quantification of an extent of a predetermined disease based on the 3-D image data for the 3-D image to create a ground truth for the 2-D images, and using each of the quantifications and the 2-D image data for each of the 2-D images to train the predictive machine learning system to be able to predict a quantitative extent of the predetermined disease in a patient based on a received 2-D patient image.

In another embodiment, a disease assessment method is provided that includes receiving 2-D patient image data representing a 2-D image of a patient, and providing the 2-D patient image data to a predictive machine learning system and using the predictive machine learning system and the 2-D patient image data to quantify an extent of a predetermined disease in the patient. The predictive machine learning system in this embodiment has been previously trained using: (i) 3-D image data for each of a plurality of 3-D images obtained from a plurality of subjects, (ii) 2-D image data for each of a plurality of 2-D images obtained from the plurality of subjects, wherein each of the 2-D images is associated with a corresponding one of the 3-D images and is captured at the same time as the corresponding one of the 3-D images or within a certain predetermined time frame of capturing the corresponding one of the 3-D images, and (iii) a ground truth for the 2-D images comprising for each of the 3-D image a quantification of an extent of the predetermined disease based on the 3-D image data for the 3-D image.

In yet another embodiment, a disease assessment system is provided that includes a computing device implementing a predictive machine learning system, the computing device having a processor apparatus structured and configured to receive 2-D patient image data representing a 2-D image of a patient, and use the predictive machine learning system and the 2-D patient image data to quantify an extent of a predetermined disease in the patient. The predictive machine learning system in this embodiment has been previously trained using (i) 3-D image data for each of a plurality of 3-D images obtained from a plurality of subjects, (ii) 2-D image data for each of a plurality of 2-D images obtained from the plurality of subjects, wherein each of the 2-D images is associated with a corresponding one of the 3-D images and is captured at the same time as the corresponding one of the 3-D images or within a certain predetermined time frame of capturing the corresponding one of the 3-D images, and (iii)

a ground truth for the 2-D images comprising for each of the 3-D images a quantification of an extent of the predetermined disease based on the 3-D image data for the 3-D image.

DETAILED DESCRIPTION OF EXEMPLARY EMBODIMENTS

Figure 1:
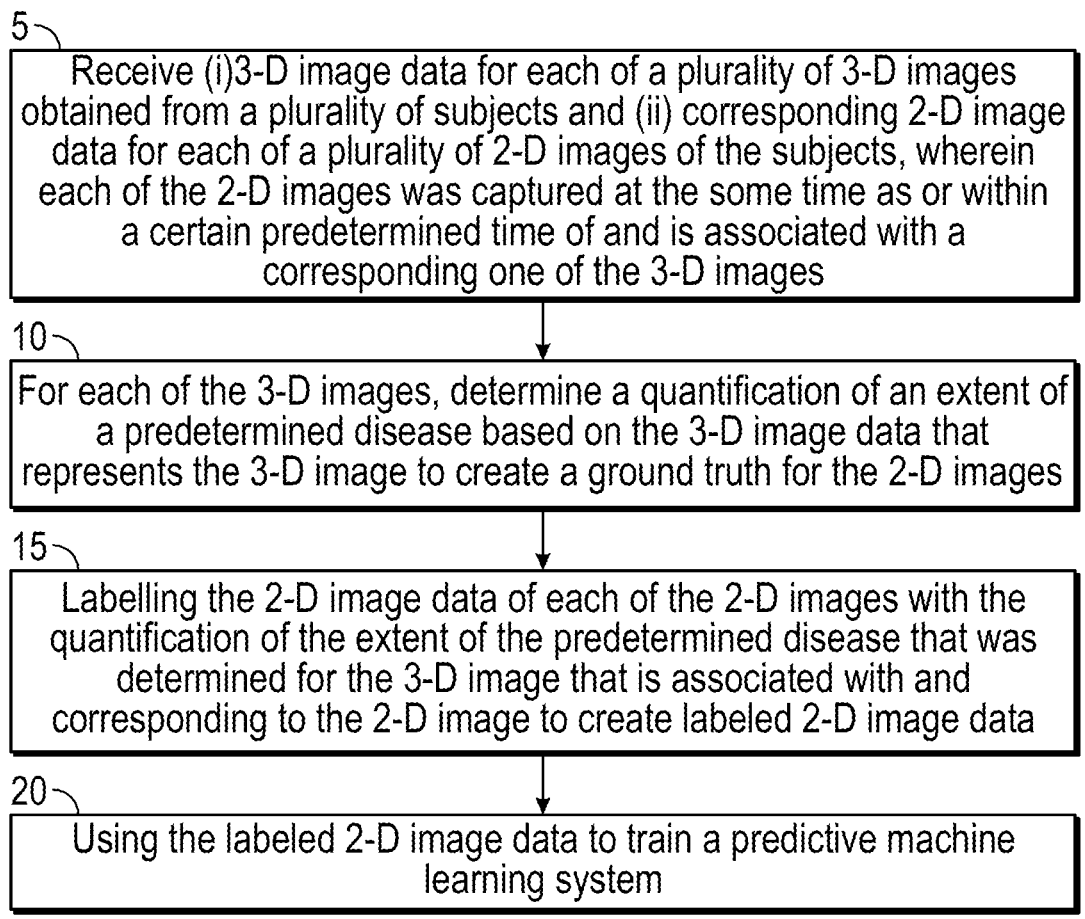
FIG. 1 is a flowchart illustrating a method of training a machine learning system according to an exemplary embodiment of the disclosed concept.

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, the term "number" shall mean one or an integer greater than one (i.e., a plurality).

As used herein, the terms "component" and "system" are intended to refer to a computer related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

As used herein, the term "deep learning" shall mean a class of machine learning algorithm that uses multiple layers to progressively extract higher level features from the raw input.

As used herein, the term "deep neural network" shall mean a deep learning artificial neural network with multiple layers between the input and output layers.

As used herein, the term "convolutional neural network" shall mean a class of deep neural network that employs a mathematical operation called convolution (a specialized kind of linear operation) in at least one layer.

As used herein, the term "deep belief network" shall mean a class of deep neural network that includes a number of hidden layers connected together consecutively (if multiple hidden layers are employed), where each hidden layer includes a restricted Boltzmann machine having neurons whose connections form a complete bipartite graph.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject invention. It will be evident, however, that the disclosed concept can be practiced without these specific details without departing from the spirit and scope of this innovation.

In the exemplary embodiment, the disclosed concept provides a machine learning based system and method for maximizing the potential of 2-D images, such as CXR images, to accurately diagnose and characterize the presence of disease, such as emphysema and pneumonia. In one particular embodiment, the present inventors investigated whether and to what extent 2-D CXR images can be explored to accurately quantify the extent of emphysema. In such an embodiment, valuable quantitative abilities are added to CXR to improve its diagnostic performance. To develop the disclosed concept, in the exemplary embodiment, the present inventors leveraged the CT scans in a cohort of COPD acquired on 753 participants to generate a reliable and sophisticated ground truth related to emphysema, namely the percentage of lung voxels with a Hounsfield (HU) value below a specific threshold (e.g., <−950 HU). The 2-D scout images acquired along with the CT scans are, in this exemplary embodiment, used as an alternative to 2-D CXR images. A classical convolutional neural network (CNN) is used to quantitatively assess the extent of the emphysema depicted on the scout images. In the exemplary embodiment, a CNN architecture known as VGG19 (to perform logistic regression) is used, although it will be appreciated that other architectures may also be used within the scope of the disclosed concept. The prediction performance was evaluated by the agreement between the computerized results and the ground-truth automatically obtained from the corresponding CT scans.

FIG. 1 is a flowchart illustrating a method of training a machine learning system, such as, without limitation, a deep learning system (e.g., a deep neural network, a convolutional neural network, or a deep belief network) according to an exemplary embodiment of the disclosed concept. The method begins at step 5, wherein a computer system receives (i) 3-D image data (e.g., CT image data or MRI image data) for each of a plurality of 3-D images obtained from a plurality of subjects and (ii) corresponding 2-D image data (e.g., 2-D CT scout image data) for each of a plurality of 2-D images of the same subjects, wherein each of the 2-D images was captured at the same time as and is associated with a corresponding one of the 3-D images. Thus, following step 5, each 3-D image will be paired with a corresponding 2-D image that was obtained from the same subject at the same time. Next, at step 10, for each of the 3-D images, a quantification of an extent of a predetermined disease, such as emphysema, is determined (automatically by the computer system) based on the 3-D image data that represents the 3-D-image in order to create a ground truth for the 2-D images that were received. In the exemplary embodiment, the quantification for each 3-D image comprises the percentage of lung voxels with a Hounsfield (HU) value below a specific threshold (e.g., <−950 HU). Then, at step 15, the 2-D image data of each of the 2-D images is labeled with the quantification that was determined for the 3-D image that is associated with and corresponds to the 2-D image. Thus, following step 10, each 2-D image will have associated with it a quantified extent of the predetermined disease that is based on and automatically obtained from the corresponding 3-D image data. Step 15 thus results in the creation of labeled 2-D image data. Then, at step 20, the labeled 2-D image data is used to train a predictive machine learning algorithm system using any known or hereafter developed methodology.

Figure 2:
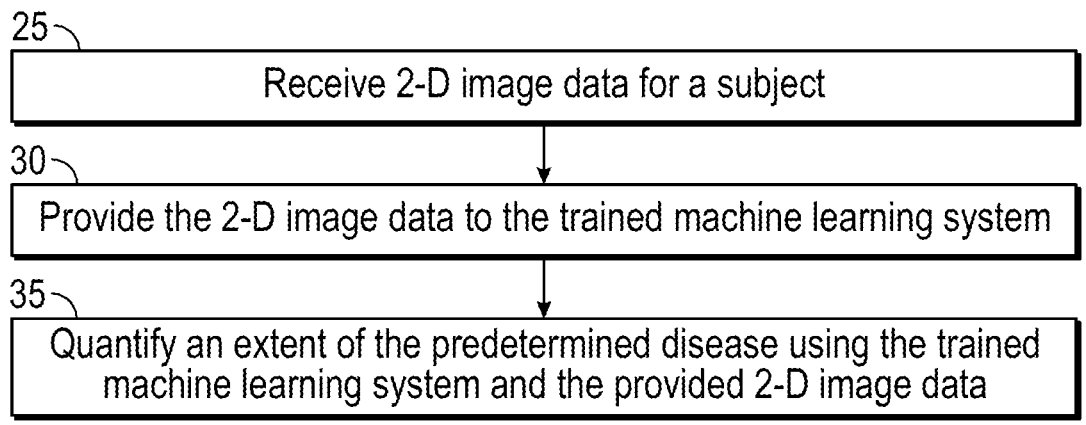
FIG. 2 is a flowchart illustrating a method of assessing the extent of a predetermined disease using 2-D images and the trained machine learning system of FIG. 1.

FIG. 2 is a flowchart illustrating a method of assessing the extent of a predetermined disease, such as emphysema, using 2-D images and the trained machine learning system of FIG. 1. The method begins at step 25, wherein 2-D image data, such as CXR data or scout image data, is received for the subject in question (i.e., a patient being assessed). Next, at step 30, the received to 2-D image data is provided to the trained machine learning system. Then, at step 35, the extent of the predetermined disease is quantified using the trained machine learning system and the provided 2-D image data.

Figure 3:
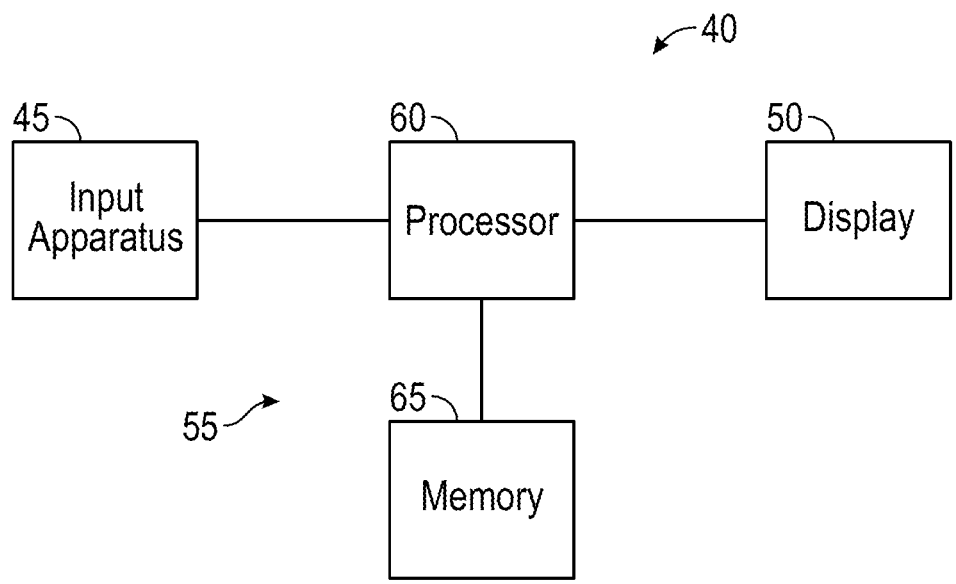
FIG. 3 is a block diagram of a computing device according to one particular exemplary embodiment of the disclosed concept in which one or both of the methods of FIGS. 1 and 2 may be implemented.

FIG. 3 is a block diagram of computing device 40 according to one particular exemplary embodiment of the disclosed concept in which one or both of the methods of FIGS. 1 and 2 may be implemented. As seen in FIG. 3, the exemplary computing device 40 is a PC or laptop computer and includes an input apparatus 45 (which in the illustrated embodiment is a keyboard), a display 50 (which in the illustrated embodiment is an LCD), and a processor apparatus 55. A user is able to provide input into processor apparatus 55 using input apparatus 45, and processor apparatus 55 provides output signals to display 50 to enable display 50 to display information to the user, such as, without limitation, the quantification of disease extent generated using the method of the disclosed concept. Processor apparatus 55 comprises a processor 60 and a memory 65. Processor 60 may be, for example and without limitation, a microprocessor (µP), a microcontroller, or some other suitable processing device, that interfaces with memory 65. Memory 65 can be any one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory. Memory 65 has stored therein a number of routines that are executable by processor 60. One or more of the routines implement (by way of computer/processor executable instructions) at least one embodiment of the methods discussed in detail herein for training a machine learning system or determining a quantification of disease extent as described herein. In particular, in the exemplary embodiment, the one or more routines implement one or more embodiments of a deep learning system as described herein.

One particular exemplary embodiment of the disclosed concept will now be described in more detail for illustrative purposes. It will be understood, however, that this is meant to be exemplary only, and that other implementations of the disclosed concept are contemplated.

In this exemplary embodiment, a study cohort consisted of 753 participants in an NIH-sponsored Specialized Center for Clinically Oriented Research (SCCOR) in COPD at the University of Pittsburgh. The inclusion criteria for enrollment were age >40 years, current or former smokers with at least a 10 pack-year history of tobacco exposure. The SCCOR subjects completed pre- and post-bronchodilator spirometry and plethysmography, measurement of lung diffusion capacity, a chest CT examination, and demographic and medical history questionnaires. All subjects had a baseline CT scan. A subset of the subjects had undergone repeat chest CT exams. Specifically, 385 subjects had a 2-year follow-up CT scan, 313 subjects had a 6-year follow-up CT scan, and 75 subjects had a 10-year follow-up CT scan. The demographic information of the subjects is summarized in Table 1 below.

TABLE 1

|  | SCCOR (n = 753) |
|---|---|
| Age, year (SD) | 64.7 (7) |
| Male, n (%) | 414 (54.7) |
| Race | |
| White, n (%) | 708 (94.0) |
| Black, n (%) | 34 (4.5) |
| Other, n (%) | 11 (1.5) |
| FEV1, % predicted (SD) | 82.3 (21.3) |
| FEV1/FVC, % (SD) | 60.6 (17.9) |
| Five-category classification | |
| Without COPD | 258 (T: 208, V: 25, I: 25) |
| GOLD I | 146 (T: 116, V: 15, I: 15) |
| GOLD II | 210 (T: 168, V: 21, I: 21) |
| GOLD III | 77 (T: 61, V: 8, I: 8) |
| GOLD IV | 62 (T: 50, V: 6, I: 6) |

The dataset includes 495 participants with COPD as defined by the Global Initiative for Obstructive Lung Disease (GOLD) [2, 20] and 258 participants without airflow obstruction (Table 1).

The involved chest CT examinations were acquired on a 64-detector CT scanner (LightSpeed VCT, GE Healthcare, Waukesha, WI, USA) with subjects holding their breath at end inspiration without the use of radiopaque contrast. Scans were acquired using a helical technique at the following parameters: 32×0.625 mm detector configuration, 0.969 pitch, 120 kVp tube energy, 250 mA tube current, and 0.4-s gantry rotation (or 100 mAs). Images were reconstructed to encompass the entire lung field in a 512×512 pixel matrix using the GE "bone" kernel at 0.625-mm section thickness and 0.625-mm interval. Pixel dimensions ranged from 0.549 to 0.738 mm, depending on participant body size. The "bone" kernel was used because of its ability to visualize both the parenchyma and airways. When performing the CT scans, 2D scout radiographs were typically acquired in advance to display and determine the body location or baseline where the subsequent slice images will be obtained. In the present cohort, the acquired scout images had a consistent matrix of 888×733 and a consistent pixel size of 0.5968×0.5455 mm2. Only the CT scans with the scout radiographs, including the follow-up scans, were used for the machine learning and evaluation purpose in this implementation. Totally, there were 1,446 paired CT scans and scout radiographs that included the baselines and the follow-ups.

To quantify the extent of emphysema, firstly the right and left lung regions were identified using an automated lung volume segmentation algorithm. Then, a threshold of −950 Hounsfield unit (HU), which is a common threshold used to identify areas of the lung with a low computed attenuation often associated with emphysema, was applied to the segmented lungs. The extent of emphysema was defined as the percentage of low attenuation areas (% LAA) relative to the total lung volume or the right/left lung volume. To reduce the overestimation of the percentage of emphysema possibly caused by image noise or artifact, small clusters of pixels were removed (the −950 HU thresholds). Considering that in-plane image pixel size ranges from approximately 0.55 mm to 0.74 mm, a relatively small threshold was selected, 3 mm2 (4~5 pixels), for discarding the image noise or artifacts below this threshold.

CNN-based deep learning technology has gained significant attention due to its remarkable performance for various medical image analysis problems, including classification, detection, segmentation, and registrations. The unique strength of CNN is its ability to automatically learn specific features (or feature map) by repeatedly applying the convolutional layers to an image. In architecture, a CNN is typically formed by several building blocks, including convolution layers, activation functions, pooling layers, batch normalization layers, flatten layers, and fully connected (FC) layers. In this exemplary embodiment, a classical CNN architecture called "VGG19" is used to perform logistic regression. The objective is to predict the continuous values of the emphysema extent from scout radiographs. The regression deep learning network is almost the same as those used for classification purposes. The differences lie in (1) the regression network uses a fully connected regression layer with linear or sigmoid activations, while the later uses Softmax activation function and (2) the deep learning-based regression typically uses the mean absolute error (MAE) or mean squared error (MSE) as the loss function, while the classification used binary or categorical cross-entropy as the loss function.

In this particular implementation, several procedures were used to alleviate the requirement of deep learning for a large dataset: First, a deep learning-based algorithm described in Liu H, Wang L, Nan Y, Jin F, Wang Q, Pu J. *SDFN: Segmentation-based deep fusion network for thoracic disease classification in chest X-ray images*, Comput Med Imaging Graph. 2019; 75:66-73, was used to segment the lung regions depicted on the scout radiographs. Second, based on the center of the identified lung regions, a square box with a dimension of 400×400 mm2 was used to crop the lung regions. The cropped lung regions were consistently resized to 512×512 pixels. Second, based on the maximum and the minimum values of the scout radiographs, the intensity of the images was scaled into a range of [0, 255]. Third, the pre-trained ImageNet weight for VGG19 was used to transfer the learning. The transfer learning can not only improve the learning efficiency but also reduce the requirement for a large and diverse dataset.

Furthermore, to develop the deep learning-based regression model, the collected cases were split into three sub-groups at the patient level, namely training, internal validation, and independent test sets in a radio of 8:1:1 (Table 1). To deal with the data imbalance, which could significantly lead to the bias and incorrect assessment of the prediction model, the minority groups were over-sampled for regression. First, the values of the extent of the emphysema by 5% were binned in the training and internal validation sets. Second, the cases in the bins with a lower number of cases was oversampled to assure their equal distribution with the bin with the maximum number of cases.

When training the models of this exemplary embodiment, the training and internal validation subgroups listed in Table 1 were used. The batch size was set at 8. To improve the data diversity and the reliability of the models, the 2D images were augmented via geometric and intensity transformations, such as rotation, translation, vertical/horizontal flips, intensity shift [−10, 10], smoothing (blurring) operation, and Gaussian noises. The initial learning rate was set as 0.0001 and would be reduced by a factor of 0.5 if the validation performance did not increase in two epochs. Adam optimizer was used, and the training procedure would stop when the validation performance of the current epoch did not improve compared to the previous fifteen epochs. Three models were trained separately for assessing the extent of the emphysema from the scout radiographs at the entire lung level, the right lung level, and the left lung level.

Two performance metrics were used to assess the performance of the developed prediction models on the independent testing dataset, among which no image was involved in the training. The first one was R-squared (R2), which is the proportion of variation in the outcome that is explained by the predictor variables. The higher the R2, the better the prediction model. The R2 was also adjusted. The second one is MAE that is the average absolute difference between the predicted outcomes and the measures obtained from the CT scans. The performance metrics were computed separately for the entire lung, the right lung, and the left lung. A p-value of less than 0.05 is considered statistically significant.

The experimental results on the independent test set are summarized in Table 2 below. At the entire lung level, the developed prediction model achieved an MAE of 2.89±2.58%, an R2 of 0.751, and an adjusted R2 of 0.749. The performance of the model was better for assessing the extent of emphysema in the right lungs (MAE=3.89±3.81%) than in the left lungs (MAE=4.92±4.20%). For the cases without COPD, the MASE was 2.30±1.80%, the R2 was 0.577, and the adjusted R2 was 0.566. The prediction model had the best performance for the cases with the most severe COPD (MAE=1.39±0.89%) and the worst performance for the cases with mild COPD (MAE=3.55±3.05%).

TABLE 2

| sub-groups | MAE (%) | R-square (R2) | Adjusted R-square |
| --- | --- | --- | --- |
| The entire lung | 2.89 ± 2.58 | 0.751 | 0.749 |
| The left lung | 4.92 ± 4.20 | 0.433 | 0.428 |
| The right lung | 3.89 ± 3.81 | 0.622 | 0.618 |
| Emphysema severity | | | |
| Without COPD | 2.30 ± 1.80 | 0.577 | 0.566 |
| GOLD I | 3.55 ± 3.05 | 0.324* | 0.290* |
| GOLD II | 1.79 ± 3.16 | 0.464 | 0.445 |
| GOLD III | 2.32 ± 2.14 | 0.832 | 0.808 |
| GOLD IV | 1.39 ± 0.89 | 0.956 | 0.947 |

*p = 0.006, all other p < 0.001

Thus, in short, the disclosed concept provides a novel method to innovatively quantify the extent of emphysema from 2-D images, such as CXR images, by using the quantitative results based on volumetric CT as the ground truth for a deep learning solution. As described, experiments on a COPD cohort demonstrated the feasibility of the disclosed concept and the very promising performance of the developed computer solution.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of training a predictive machine learning system for of lung disease, comprising:
   receiving in a computer system (i) 3-D image data for each of a plurality of 3-D images obtained from a plurality of subjects, and (ii) 2-D image data for each of a plurality of 2-D images obtained from the plurality of subjects;
   for each of the 3-D images, determining in the computer system a quantification of an extent of lung disease based on the 3-D image data for the 3-D image to create a ground truth for the 2-D images, wherein the quantification of the extent of lung disease comprises a percentage of lung low attenuation areas relative to total lung volume in the 3-D image based on a predetermined Hounsfield unit threshold; and
   using each of the quantifications and the 2-D image data for each of the 2-D images to train the predictive machine learning system to be able to predict a quantitative extent of lung disease in a patient based on a received 2-D patient image.

2. The method according to claim 1, wherein the using each of the quantifications and the 2-D image data for each of the 2-D images to train the predictive machine learning system comprises, for each of the 2-D images, labelling the 2-D image data of the 2-D image with the quantifications that was determined for the 3-D image that is associated with the 2-D image to create labeled 2-D image data, and using the labeled 2-D image data to train the predictive machine learning system.

3. The method according to claim 1, wherein the predictive machine learning system is a deep learning system.

4. The method according to claim 3, wherein the deep learning system is a deep neural network.

5. The method according to claim 4, wherein the deep learning network is a convolution neural network.

6. The method according to claim 4, wherein the deep learning network is a deep belief network.

7. The method according to claim 1, wherein the 3-D images are each a CT image or an MRI image.

8. The method according to claim 1, wherein each of the 3-D images is a CT image and each of the plurality of 2-D images is a 2-D CT scout radiograph.

9. The method according to claim 1, wherein the received patient 2-D image is a 2-D x-ray image.

10. The method according to claim 1, wherein each quantification comprises a percentage of lung voxels with a Hounsfield (HU) value below the predetermined Hounsfield unit threshold.

11. A computer program product, comprising a non-transitory computer usable medium having a computer readable program code embodied therein, the computer readable program code being adapted and configured to be executed to implement a method of training a predictive machine learning system for lung disease assessment according to claim 1.

12. The method according to claim 1, wherein each of the 2-D images is associated with but not derived form a corresponding one of the 3-D images and is captured by an imaging apparatus at the same time as the corresponding one of the 3-D images or within a certain predetermined time frame of capturing the corresponding one of the 3-D images.

13. The method according to claim 1, wherein the predetermined Hounsfield unit threshold is a −950 Hounsfield unit threshold.

14. The method according to claim 1, wherein the lung disease is emphysema.

15. A lung disease assessment method, comprising:
   receiving 2-D patient image data representing a 2-D image of a patient, and
   providing the 2-D patient image data to a predictive machine learning system and using the predictive machine learning system and the 2-D patient image data to quantify an extent of lung disease in the patient, wherein the predictive machine learning system has been previously trained using: (i) 3-D image data for each of a plurality of 3-D images obtained from a plurality of subjects, (ii) 2-D image data for each of a plurality of 2-D images obtained from the plurality of subjects; and (iii) a ground truth for the 2-D images comprising for each of the 3-D images a quantification of an extent of lung disease based on the 3-D image data for the 3-D image, wherein the quantification of the extent of lung disease comp percentage of lung low attenuation areas relative to total lung volume in the 3-D image based on a predetermined Hounsfield unit threshold.

16. The method according to claim 15, wherein the predictive machine learning system is a deep learning system.

17. The method according to claim 16, wherein the deep learning system is a deep neural network.

18. The method according to claim 17, wherein the deep learning network is a convolution neural network.

19. The method according to claim 17, wherein the deep learning network is a deep belief network.

20. The method according to claim 15, wherein the 3-D images are each a CT image or an MRI image.

21. The method according to claim 15, wherein each of the 3-D images is a CT image and each of the plurality of 2-D images is a 2-D CT scout radiograph.

22. The method according to claim 15, wherein the 2-D image of the patient is a 2-D x-ray image.

23. The method according to claim 15, wherein each quantification comprises a percentage of lung voxels with a Hounsfield (HU) value below the predetermined Hounsfield unit threshold.

24. A computer program product, comprising a non-transitory computer usable medium having a computer readable program code embodied therein, the computer readable program code being adapted to be executed to implement a lung disease assessment method as recited in claim 15.

25. The method according to claim 15, wherein each of the 2-D images is associated with but not derived form a corresponding one of the 3-D images and is captured by an imaging apparatus at the same time as the corresponding one of the 3-D images or within a certain predetermined time frame of capturing the corresponding one of the 3-D images.

26. The method according to claim 15, wherein the predetermined Hounsfield unit threshold is a −950 Hounsfield unit threshold.

27. The method according to claim 15, wherein the lung disease is emphysema.

28. A lung disease assessment system, comprising:
   a computing device implementing a predictive machine learning system, the computing device having a processor apparatus structured and configured to:

receive 2-D patient image data representing a 2-D image of a patient; and use the predictive machine learning system and the 2-D patient image data to quantify an extent of lung disease in the patient, wherein the predictive machine learning system has been previously trained using (1) 3-D image data for each of a plurality of 3-D images obtained from a plurality of subjects, (ii) 2-D image data for each of a plurality of 2-D images obtained from the plurality of subjects, and (iii) a ground truth for the 2-D images comprising for each of the 3-D images a quantification of an extent of lung disease based on the 3-D image data for the 3-D image, wherein the qualification of the extent of lung disease comprises a percentage of lung low attenuation areas relative to total lung volume in the 3-D image based on a predetermined Hounsfield unit threshold.

29. The system according to claim 28, wherein the predictive machine learning system is a deep learning system.

30. The system according to claim 29, wherein the deep learning system is a deep neural network.

31. The system according to claim 30, wherein the deep learning network is a convolution neural network.

32. The system according to claim 30, wherein the deep learning network is a deep belief network.

33. The system according to claim 28, wherein the 3-D images are each a CT image or an MRI image.

34. The system according to claim 28, wherein each of the 3-D images is a CT image and each of the plurality of 2-D images is a 2-D CT scout radiograph.

35. The system according to claim 28, wherein the 2-D image of the patient is a 2-D x-ray image.

36. The system according to claim 28, wherein each quantification comprises a percentage of lung voxels with a Hounsfield (HU) value below the predetermined Hounsfield unit threshold.

37. The system according to claim 28, wherein each of the 2-D images is associated with but not derived form a corresponding one of the 3-D images and is captured by an imaging apparatus at the same time as the corresponding one of the 3-D images or within a certain predetermined time frame of capturing the corresponding one of the 3-D images.

38. The system according to claim 28, wherein the predetermined Hounsfield unit threshold is a −950 Hounsfield unit threshold.

39. The system according to claim 28, wherein the lung disease is emphysema.

* * * * *

UNITED STATES PATENT AND TRADEMARK OFFICE
CERTIFICATE OF CORRECTION

| | | |
|---|---|---|
| PATENT NO. | : 12,307,657 B2 | Page 1 of 1 |
| APPLICATION NO. | : 17/348840 | |
| DATED | : May 20, 2025 | |
| INVENTOR(S) | : Jiantao Pu | |

It is certified that error appears in the above-identified patent and that said Letters Patent is hereby corrected as shown below:

In the Claims

Column 9, Claim 1, Line 10, add the word --assessment-- after the word "for".

Column 10, Claim 15, Line 24, change the word "comp" to --comprises-- and add the word --a-- before "percentage".

Signed and Sealed this
Fifteenth Day of July, 2025

Coke Morgan Stewart
*Acting Director of the United States Patent and Trademark Office*